United States Patent
Kiy et al.

(10) Patent No.: US 7,217,550 B2
(45) Date of Patent: May 15, 2007

(54) NUCLEOTIDE-SUGAR-SYNTHESIZING ENZYMES FROM NONPARASITIC PROTISTS

(75) Inventors: Thomas Kiy, Frankfurt (DE); Lothar Elling, Aachen (DE); Maria Regina Kula, Niederzier-Hambach (DE)

(73) Assignee: Nutrinova, Nutrition Specialties & Food Ingredients, GmbH, Frankfurt am Main (DE)

( * ) Notice: Subject to any disclaimer, the term of this patent is extended or adjusted under 35 U.S.C. 154(b) by 448 days.

(21) Appl. No.: 10/436,382

(22) Filed: May 12, 2003

(65) Prior Publication Data

US 2003/0207433 A1 Nov. 6, 2003

Related U.S. Application Data

(62) Division of application No. 08/796,697, filed on Mar. 3, 1997, now Pat. No. 6,143,539.

(30) Foreign Application Priority Data

Mar. 5, 1996 (DE) .............. P 196 08 268

(51) Int. Cl.
*C12N 9/12* (2006.01)
(52) U.S. Cl. .............. 435/194; 435/258.1; 435/947
(58) Field of Classification Search .............. None
See application file for complete search history.

(56) References Cited

OTHER PUBLICATIONS

Ishihara et al., J. of Biological Chemistry, vol. 243, No. 6, p. 1110-1115, 1968.*
Niittymäki et al, "Cloning and expression of murine enzymes involved in the salvage pathway of GDP- L- fucose"; Eur. J. Biochem., (2004), 271, 78-86.
Pastuszak et al, "GDP- L- fucose Pyrophosphorylase": The Journal of Biological Chemistry, (1998), vol. 273, No. 46, Issue of Nov. 13, pp. 30165-30174.
Journal of Bacteriology (1974) 120(3), 1151-1157.
J Biochem (1978) 83(3): 693-698.
Lee et al., J. Biochem. (Tokyo) 86, p. 923-928, 1979.
Kamogawa et al., J Biochem. (Tokyo), 57, p. 758-765 1965.
Pernin et al. J. Protozool. (1971), 18(1), 115-119.
Daran et al., European J. Biochem., 233(2) 520-530, 1995.
Field et al., Glycobiology, 5(5): 463-472, 1995.
Macechko et al., Molecular & Biochemical Parasitology, 56: 301-310, 1992.
Rich et al., Molecular & Biochemical Parasitology, 7: 173-182, 1983.
Takeuchi et al., Experimental Parasitology, 43: 115-121, 1977.
Raizada et al., J. Protozool, 18(1): 115-119, 1971.
Rudick et al., J. Biol. Chem., 249(24): 7832-7840; 1974.
Cook et al., Archives of Biochem & Biophys., 127:72-78, 1968.
Pavlovic et al. Developmental Genetics, 9: 371-382, 1988.
Ragheb et al., Nucleic Acids Research, 15(9): 3891-3906, 1987.
Kiy et al., Applied Microbiology & Biotechnology, 37: 576-579, 1992.

* cited by examiner

*Primary Examiner*—Irene Marx
(74) *Attorney, Agent, or Firm*—Frommer Lawrence & Haug LLP

(57) ABSTRACT

The present invention relates to nucleotide-sugar-synthesizing enzymes (enzymes with nucleotidyltransferase or pyrophosphorylase activity) from nonparasitic protists, to a process for the preparation thereof and to the use thereof for preparing nucleotide-sugars. The enzymes according to the invention make possible or greatly simplify the enzymatic preparation of various nucleotide-sugars on the industrial scale from low-cost precursors. It is possible with the aid of the discovered enzymes to prepare, for example, GDP-fucose, GDP-mannose, UDP-glucose, UDP-glucosamine, UDP-galactose, UDP-galactosamine, UDP-N-acetylglucosamine and UDP-N-acetylgalactosamine in economic quantities.

6 Claims, No Drawings

NUCLEOTIDE-SUGAR-SYNTHESIZING ENZYMES FROM NONPARASITIC PROTISTS

CROSS REFERENCE TO RELATED APPLICATIONS

This application is a divisional of application Ser. No. 08/796,697, filed Mar. 3, 1997, now U.S. Pat. No. 6,143,539, which claims priority to German application no. P 196 08 268.4, filed Mar. 5, 1996. The disclosure of these applications are hereby incorporated by reference into the present application.

BACKGROUND OF THE INVENTION

The present invention relates to nucleotide-sugar-synthesizing enzymes, i.e. enzymes with nucleotidyltransferase or pyrophosphorylase activity, from nonparasitic protists, to a process for the preparation thereof and to the use thereof for preparing nucleotide-sugars.

Oligo- and polysaccharides play an important part in nature. They are of essential importance as components of glycoproteins and glycolipids in cellular communication processes and as binding sites for, for example, antibodies, lectins and hormones. They also crucially determine the physical properties of proteins such as solubility, stability and 3D structure. They furthermore act as receptors for pathological states mediated by viruses, bacteria and protists.

The recognition of the versatile functions of the carbohydrate residues in glycoconjugates is also associated with an increasing interest in synthesizing such compounds. However, because of their great complexity and the specific requirements for chemoselectivity, regioselectivity and stereoselectivity, the synthesis even of lower oligosaccharides by chemical means is extremely difficult. As the complexity of the saccharides increases there is also an increase in the difficulty of reproducing them by chemical synthesis. For this reason it is obvious to copy the biological synthetic routes and to have recourse to enzymes, which usually catalyze substrate-, regio- and stereospecific reactions, for synthesizing complex saccharides.

The oligosaccharide structures of glycoconjugates are synthesized in vivo by Leloir glycosyltransferases which require activated sugars (nucleotide-sugars) as donor substrates for the regio- and stereoselective transfer. The nucleotide-sugars are produced by nucleotidyltransferases or pyrophosphorylases (for example EC 2.7.7.9 to 2.7.7.13, 2.7.7.23, 2.7.7.29, 2.7.7.30) using nucleoside triphosphates. In this, transfer of the nucleotidyl group of a nucleoside triphosphate (NTP) to a sugar phosphate (sugar(-1-P)) is catalyzed with liberation of pyrophosphate (PPi).

The use of oligosaccharide structures as potential therapeutic agents (inhibitors, antiadhesive agents, antiinflammatory agents, immunogenic stimulators etc.) or diagnostic aids (determinants, lectin ligands) requires unrestricted synthetic access thereto.

There are in principle two possible approaches to the synthesis of oligosaccharide structures; a chemical and an enzymatic synthesis. Chemical synthesis is associated with many disadvantages because complex strategies using protective group techniques are, as a rule, time-consuming and result in only low yields. This applies equally to the chemical preparation of nucleotide-sugars. However, the costs are very high because of the elaborate synthesis and the frequently poor yields. Thus, 10 mg of chemically synthesized GDP-β-L-fucose cost about 1000 DM.

A number of glycosyl transferases are now available for enzymatic synthesis of oligosaccharide structures. More than one hundred glycosyl transferases have now been isolated from eukaryotes (Glycobiology, 1995, 5, 463). A crucial precondition for industrial synthesis is enzymatic access to the costly nucleotide-sugars. There is at present a great demand and great scientific interest therein. Thus, for example, enzymatic synthesis of GDP-β-L-fucose has not been possible on the industrial scale in the absence of a suitable enzyme system.

The object therefore is to find novel "microbial" sources which can be fermented on a large scale for obtaining nucleotide-sugar-synthesizing enzymes. Surprisingly, it has been possible in this connection to identify a group of organisms which has hitherto been completely ignored—the free-living, nonparasitic protists—as novel and promising producers of the enzymes which are sought.

Hitherto, only a few pyrophosphorylases were known from parasitic protists, either pathogens or facultative pathogens, such as, for example UDP-N-acetylglucosamine pyrophosphorylase from Giardia (Mol Biochem. Parasitol., 1992, 56, 301), UTP-hexose-1-phosphate uridyltransferase (E.C. 2.7.7.10) and UDP-glucose pyrophosphorylase from Entamoeba histolytica (Mol. Biochem. Parasitol., 1983, 7, 173 and Exp. Parasitol., 1977, 43, 115), UDP-glucose pyrophosphorylase from Hartmanella culbertsoni (J. Protozool., 1971, 18, 115) and UDP-glucose pyrophosphorylase from Acanthamoeba castellanii (J. Biol. Chem., 1974, 249, 7832).

Apart from the UDP-glucose pyrophosphoryltase from Tetrahymena pyriformis (Arch. Biochem. Biophys., 1968, 127, 72) and from Dictyostelium (J. Paulovic et al., Dev. Genet. 9, 371–382 (1988); J. A. Ragheb et al., Nucleic Acid Res. 15, 3891–3896 (1987)), astonishingly no nucleotidyl transferases have hitherto been described in free-living, nonparasitic protists.

SUMMARY OF THE INVENTION

The present invention thus relates to a nucleotide-sugar-synthesizing enzyme which is obtainable from nonpathogenic protists, with the exception of UDP-glucose pyrophosphorylase from Tetrahymena pyriformis and from Dictyostelium.

DETAILED DESCRIPTION OF THE INVENTION

The advantages of such nucleotide-sugar-synthesizing enzymes from nonpathogenic protists include:

1. The enzymes can easily be prepared in large quantities by fermentative processes.
2. One strain frequently produces several nucleotidyl transferases at the same time.
3. The enzymes are stable as a rule. The activities are retained even after freezing several times.
4. The specific activities are in some cases extremely high (see Table 1).

The enzyme according to the invention preferably has the activities of a UDP-N-acetylgalactosamine pyrophosphorylase (UDP-GalNAc-pyrophosphorylase), UDP-N-acetylglucosamine pyrophosphorylase (EC No. 2.7.7.23), GDP-fucose pyrophosphorylase (EC No. 2.7.7.30), GTP-mannose-1-phosphate guanyltransferase (EC No. 2.7.7.13), UDP-glucose pyrophosphorylase (EC No. 2.7.7.9), a UTP-galactose-1-phosphate uridyltransferase (EC No. 2.7.7.10), a UTP-xylose-1-phosphate uridyltransferase (EC No. 2.7.7.11) or a nucleoside-triphosphate-hexose-1-phosphate nucleotidyltransferase (EC No. 2.7.7.28). EC numbers according to the Enzyme Nomenclature 1992, Academic Press, Inc., San Diego, New York, Boston.

The enzyme according to the invention is preferably obtainable from protists of the classes Ciliata (for example of the genera *Tetrahymena, Paramecium, Colpidium, Colpoda, Glaucoma, Platyophrya, Vorticella, Potomacus, Pseudocohnilembus, Euplotes, Engelmaniella and Stylonichia*), of the subphylum Mastigophora (flagellates), of the classes of Phytomastigophorea (for example of the genera *Euglena, Astasia, Haematococcus* and *Crypthecodinium*), Zoomastigophorea, of the superclass Rhizopoda, of the classes Lobosea (for example of the genera *Amoeba*) and Eumycetozoea (for example of the genera *Dictyostelium and Physarum*) (systematic nomenclature based on H. Mehlhorn & A. Ruthmann, Allgemeine Protozoology [General Protozoology], 1992, Gustav Fischer Veriag Jena) or from mutants of these nonparasitic protists.

The invention furthermore relates to a process for the preparation of such a nucleotide-sugar-synthesizing enzyme.

In the process according to the invention, the protists are cultivated on axenic or chemically defined culture media containing feed organisms. The temperature in this case is in the range 15–45° C. The organisms can be chosen to be grown in the form of stationary or shake cultures, in spinner bottles or fermenters, it being possible for the fermentation to be designed preferably as batch, fed-batch or continuous fermentation.

The enzymes are preferably obtained from the biomass. The biomass can be harvested, for example, by tangential filtration, sedimentation and centrifugation. The subsequent cell disruption can be carried out, for example, as selected by means of ultrasound or Ultraturrax apparatuses, homogenizers or by freezing.

The enzyme-containing crude extracts can be used directly to prepare nucleotide-sugars. Alternatively, the enzymes can be initially be purified by chromatographic processes (for example gel filtration, ion exchange, affinity and/or hydrophobic interaction chromatography) and/or precipitations. Accordingly, the present invention also relates to the use of the enzyme according to the invention for preparing nucleotide-sugars.

Detection of nucleotide-sugar-synthesizing enzymes takes place by the so-called "nucleotidyltransferase substrate screening assay" (NUSSA) (German Patent Application No. 195 17 093.8). This assay allows the nucleotide-sugar-synthesizing enzymes to be identified by converting the product PPi resulting from the reaction by means of a PPi-dependent phosphofructokinase. The subsequent enzyme cascade results in 2 mol of NAD per mole of PPi. It is possible to differentiate between the various nucleotide-sugar-synthesizing enzymes depending on which nucleoside triphosphate and which sugar 1-phosphate is employed as substrate at the start. The principle of the NUSSA is explained by the following scheme:

Nucleotidyltransferase Substrate Screening Assay (NUSSA)

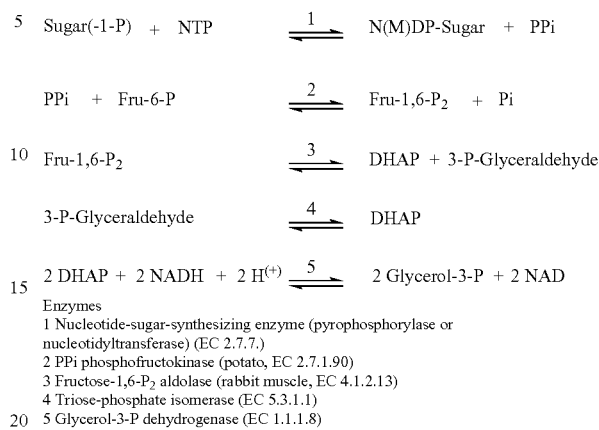

Enzymes
1 Nucleotide-sugar-synthesizing enzyme (pyrophosphorylase or nucleotidyltransferase) (EC 2.7.7.)
2 PPi phosphofructokinase (potato, EC 2.7.1.90)
3 Fructose-1,6-P$_2$ aldolase (rabbit muscle, EC 4.1.2.13)
4 Triose-phosphate isomerase (EC 5.3.1.1)
5 Glycerol-3-P dehydrogenase (EC 1.1.1.8)

The nucleotide-sugar-synthesizing enzymes can also, besides the NUSSA (Nucleotidyltransferase substrate screening assay) be identified by HPLC processes and thin-layer chromatography processes.

1. HPLC

The samples are obtained as explained, for example, in Example 1. Subsequently, a suitable dilution of the sample is introduced into a buffer system (for example 50 mM Tris/HCl) containing the appropriate nucleotide triphosphates (for example GTP, ATP) and the sugar phosphates (for example fucose 1-phosphate). The incubation can comprise, for example, 10 min at 30° C. The sugar-nucleotides (for example GDP-fucose) formed by the activity of the nucleotide-sugar-synthesizing enzymes (for example GDP-fucose pyrophosphorylase) present in the samples are then identified chromatographically by HPLC (for example on an RP$_{18}$ column), carrying out gradient elution for example with an increase in acetonitrile concentration. Solution A consists of 5 mM tetrabutylammonium hydrogen sulfate, 30 mM potassium dihydrogen phosphate and 4% acetonitrile, pH 6. Solution B consists of pure acetonitrile. A suitable gradient is, for example, 0–40% B, with flow rates preferably between 1 and 2 ml/min. Measurement is carried out by UV detector and integrator. It is also possible to use tetrabutylammonium bromide as alternative to tetrabutylammonium hydrogen sulfate.

2. Thin-layer Chromatography

If the concentration of the sugar-nucleotides formed is sufficiently high, detection is also possible by TLC. A suitable mobile phase is, for example acetonitrile/0.1 M NH$_4$Cl in the ratio 6:4. The spray reagent which can be used is a solution of naphthoresorcinol (20 mg), diphenylamine (40 mg), ethanol (10 ml) and sulfuric acid (400 µl). The plates used are TLC glass plates, 0.25 mm of silica gel.

The present invention furthermore relates to the use of nonparasitic protists which produce nucleotide-synthesizing enzymes for the preparation of nucleotide-sugars.

EXAMPLES

1. *Tetrahymena thermophila*: 21 Erlenmeyer flasks each containing 500 ml of skimmed milk medium (2% skimmed milk powder, 0.5% yeast extract, 0.003% Sequestrene; according to Kiy & Tiedtke, 1992, Appl.

Microbiol. Biotechnol., 37, 576) were incubated at 30° C. and 100 rpm for 48 h. The cultures were harvested at a cell density of 835,000 cells/ml in a FILTRON tangential filtration system (pore size 0.3 µm). The concentrated cell suspension was centrifuged again (SORVALL RC-5B, GSA Rotor, 10,000 rpm, 10 min). The cell pellet was disrupted by freezing at −20° C.

After thawing, a sample was introduced at a suitable dilution into the NUSSA. Enzymes which synthesized UDP-glucose, UDP-N-acetylglucosamine, UDP-galactose, UDP-galactosamine, UDP-N-acetylgalactosamine, GDP-fucose and GDP-mannose were identified in the crude extract (Tab. 1). Surprisingly, some of these enzymes (UDP-glucose-, UDP-N-acetyl-glucosamine-,UDP-galactose-, UDP-N-acetylgalactosamine- and GDP-mannose-synthesizing enzymes) were also present in the cell-free culture filtrate (Tab.2).

2. *Tetrahymena thermophila*: T. thermophila is cultivated in a 2l stirred fermenter (BRAUN BIOTECH INTERNATIONAL) at 30° C. Stirring was effected by a paddle impeller, the pO$_2$ was kept at 30% and the pH was kept at 7.0. The medium used was the abovementioned skimmed milk medium.

After the stationary phase was reached, 5-fold concentrated skimmed milk medium was repeatedly added. After 10 days, the cells were harvested at a cell density of 7,000,000 cells/ml, and further processed, as described under 1.

The same enzymes as in 1 were identified by the NUSSA (Tab. 3).

The following enzymes were found in the cell-free culture filtrate: (see Tab. 4).

3. *Tetrahymena setosa*: The cells were cultivated as described in 1. The culture was harvested at a cell density of 1,320,000 cells/ml.
UDP-Glucose-, UDP-glucosamine-, UDP-N-acetylglucosamine-, UDP-galactose-,
UDP-galactosamine-, UDP-N-acetylgalactosamine-, GDP-fucose- and
GDP-mannose-synthesizing enzymes were identified in the crude extract (Tab.5).
UDP-Glucose-, UDP-glucosamine-, UDP-N-acetylglucosamine-, UDP-galactose-,
UDP-N-acetylgalactosamine-, GDP-fucose- and GDP-mannose-synthesizing enzymes were detectable in the cell-free culture filtrate (Tab. 6).

4. *Tetrahymena pyriformis*: T. pyriformis was cultivated on PPYS medium (1% proteose peptone, 0.1% yeast extract, 0.003% Sequestrene) at 27° C. and 60 rpm. The cultures were harvested at a cell density of 500,000 cells/ml, and were further processed, as described under 1.
UDP-Glucose-, UDP-N-acetylglucosamine-, UDP-galactose-,
UDP-N-acetylgalactosamine-, GDP-fucose- and GDP-mannose-synthesizing enzymes were identified in the crude extract (Tab. 7).
Additionally found in the cell-free culture filtrate were UDP-glucosamine- and
UDP-galactosamine-synthesizing enzymes (Tab. 8).

5. *Colpidium campylum*: This ciliate was incubated on skimmed milk medium at 25° C. and 60 rpm for 3 d. The culture was harvested at a cell density of 250,000 cell/ml, and further processed, as described under 1.
UDP-Glucose-, UDP-glucosamine-, UDP-N-acetylglucosamine-, UDP-galactose-,
UDP-galactosamine-, UDP-N-acetylgalactosamine-, GDP-fucose- and
GDP-mannose-synthesizing enzymes were identified in the crude extract (Tab. 9).
UDP-Glucose-, UDP-N-acetylglucosamine-, UDP-galactose- and
GDP-mannose-synthesizing enzymes were detected in the cell-free culture filtrate (Tab. 10).

6. *Potomacus pottsi*: P. pottsi was incubated on skimmed milk medium as stationary culture at 25° C. for 8 d. After the cells had reached a density of 160,000/ml, the culture was worked up as described under 1.
The crude extract contained UDP-glucose-, UDP-glucosamine-,
UDP-N-acetylglucosamine-, UDP-galactose-, UDP-galactosamine-,
UDP-N-acetylgalactosamine-, GDP-fucose- and GDP-mannose- synthesizing enzymes (Tab.11).
Also detectable in the culture filtrate were UDP-glucose-, UDP-glucosamine-,
UDP-N-acetylglucosamine-, UDP-galactose-, UDP-galactosamine- and
UDP-N-acetylgalactosamine-synthesizing enzymes (Tab. 12).

7. *Euglena gracilis*: This flagellate was incubated in medium 9 (1 g/l Na acetate, 1 g/l meat extract, 2 g/l Bacto tryptone, 2 g/l yeast extract, 30 ml/l soil stock solution) as stationary culture at 25° C. for 7 d. The cells were harvested at a cell density of 1,230,000 cells/ml as described under 1. The cells were disrupted with an UltraTurrax.
UDP-Glucose-, UDP-glucosamine-, UDP-N-acetylglucosamine-, UDP-galactose-,
UDP-N-acetylgalactosamine-, GDP-fucose- and GDP-mannose-synthesizing enzymes were identified in the crude extract (Tab. 13).
UDP-Glucose-, UDP-N-acetylglucosamine-, UDP-galactose-,
UDP-galactosamine-, UDP-N-acetylgalactosamine-, GDP-fucose- and
GDP-mannose-synthesizing enzymes were found in the culture filtrate (Tab. 14).

TABLE 1

| Enzyme: | NUSSA Crude extract, protein: 22.3 mg/ml | | | | |
|---|---|---|---|---|---|
| Source: | *Tetrahymena thermophila* | | | | |
| Class: | Ciliate | | | | |
| Specific activity (mU/mg) | | | | | |
|  | UTP | CTP | dTTP | ATP | GTP |
| Glc-1-P | 440.00 | | | | |
| GlcN-1-P | 0.00 | | | | |
| GlcNAc-1-P | 130.00 | | | | |
| GlcA-1-P | | | | | |
| Gal-1-P | 240.00 | | | | |
| GalN-1-P | 15.00 | | | | |
| GalNAc-1-P | 47.00 | | | | |
| GalA-1-P | | | | | |
| Xyl-1-P | | | | | |
| β-L-Fuc-1-P | | | | | 26.00 |
| Man1-P | | | | | 38.00 |

TABLE 2

| Enzyme: | NUSSA Filtrate, protein: 0.065 mg/ml | | | | |
|---|---|---|---|---|---|
| Source: | *Tetrahymena thermophila* | | | | |
| Class: | Ciliate | | | | |
| Specific activity (mU/mg) | | | | | |
|  | UTP | CTP | dTTP | ATP | GTP |
| Glc-1-P | 92.00 | | | | |
| GlcN-1-P | 0.00 | | | | |

TABLE 2-continued

| | UTP | CTP | dTTP | ATP | GTP |
|---|---|---|---|---|---|
| GlcNAc-1-P | 62.00 | | | | |
| GlcA-1-P | | | | | |
| Gal-1-P | 46.00 | | | | |
| GalN-1-P | 0.00 | | | | |
| GalNAc-1-P | 1.50 | | | | |
| GalA-1-P | | | | | |
| Xyl-1-P | | | | | |
| β-L-Fuc-1-P | | | | | 00.00 |
| Man1-P | | | | | 21.50 |

TABLE 3

NUSSA
Enzyme: Crude extract, protein: 17.8 mg/ml
Source: *Tetrahymena thermophila*
Class: Ciliate
Specific activity (mU/mg)

| | UTP | CTP | dTTP | ATP | GTP |
|---|---|---|---|---|---|
| Glc-1-P | 294.00 | | | | |
| GlcN-1-P | 0.00 | | | | |
| GlcNAc-1-P | 148.31 | | | | |
| GlcA-1-P | | | | | |
| Gal-1-P | 199.44 | | | | |
| GalN-1-P | 22.47 | | | | |
| GalNAc-1-P | 41.57 | | | | |
| GalA-1-P | | | | | |
| Xyl-1-P | | | | | |
| β-L-Fuc-1-P | | | | | 3.37 |
| Man1-P | | | | | 24.16 |

TABLE 4

NUSSA
Enzyme: Filtrate, protein: 0.42 mg/ml
Source: *Tetrahymena thermophila*
Class: Ciliate
Specific activity (mU/mg)

| | UTP | CTP | dTTP | ATP | GTP |
|---|---|---|---|---|---|
| Glc-1-P | 21.43 | | | | |
| GlcN-1-P | 6.19 | | | | |
| GlcNAc-1-P | 11.43 | | | | |
| GlcA-1-P | | | | | |
| Gal-1-P | 0.00 | | | | |
| GalN-1-P | 0.00 | | | | |
| GalNAc-1-P | 0.00 | | | | |
| GalA-1-P | | | | | |
| Xyl-1-P | | | | | |
| β-L-Fuc-1-P | | | | | 0.00 |
| Man1-P | | | | | 0.00 |

TABLE 5

NUSSA
Enzyme: Crude extract, protein: 14.3 mg/ml
Source: *Tetrahymena setosa*
Class: Ciliate
Specific activity (mU/mg)

| | UTP | CTP | dTTP | ATP | GTP |
|---|---|---|---|---|---|
| Glc-1-P | 713.29 | | | | |
| GlcN-1-P | 36.36 | | | | |
| GlcNAc-1-P | 204.20 | | | | |
| GlcA-1-P | | | | | |
| Gal-1-P | 351.05 | | | | |
| GalN-1-P | 15.38 | | | | |
| GalNAc-1-P | 30.07 | | | | |
| GalA-1-P | | | | | |
| Xyl-1-P | | | | | |
| β-L-Fuc-1-P | | | | | 16.08 |
| Man1-P | | | | | 39.16 |

TABLE 6

NUSSA
Enzyme: Filtrate, protein: 0.052 mg/ml
Source: *Tetrahymena setosa*
Class: Ciliate
Specific activity (mU/mg)

| | UTP | CTP | dTTP | ATP | GTP |
|---|---|---|---|---|---|
| Glc-1-P | 48.08 | | | | |
| GlcN-1-P | 1.92 | | | | |
| GlcNAc-1-P | 15.38 | | | | |
| GlcA-1-P | | | | | |
| Gal-1-P | 23.08 | | | | |
| GalN-1-P | 0.00 | | | | |
| GalNAc-1-P | 26.92 | | | | |
| GalA-1-P | | | | | |
| Xyl-1-P | | | | | |
| β-L-Fuc-1-P | | | | | 36.54 |
| Man1-P | | | | | 19.23 |

TABLE 7

NUSSA
Enzyme: Crude extract, protein: 10.0 mg/ml
Source: *Tetrahymena pyriformis*
Class: Ciliate
Specific activity (mU/mg)

| | UTP | CTP | dTTP | ATP | GTP |
|---|---|---|---|---|---|
| Glc-1-P | 509.00 | | | | |
| GlcN-1-P | 0.00 | | | | |
| GlcNAc-1-P | 96.00 | | | | |
| GlcA-1-P | | | | | |
| Gal-1-P | 312.00 | | | | |
| GalN-1-P | 0.00 | | | | |
| GalNAc-1-P | 2.00 | | | | |
| GalA-1-P | | | | | |
| Xyl-1-P | | | | | |
| β-L-Fuc-1-P | | | | | 34.00 |
| Man1-P | | | | | 22.00 |

TABLE 8

NUSSA
Enzyme: Filtrate, protein: 0.054 mg/ml
Source: *Tetrahymena pyriformis*
Class: Ciliate
Specific activity (mU/mg)

| | UTP | CTP | dTTP | ATP | GTP |
|---|---|---|---|---|---|
| Glc-1-P | 203.70 | | | | |
| GlcN-1-P | 22.22 | | | | |
| GlcNAc-1-P | 101.85 | | | | |
| GlcA-1-P | | | | | |
| Gal-1-P | 129.63 | | | | |
| GalN-1-P | 18.52 | | | | |
| GalNAc-1-P | 55.56 | | | | |
| GalA-1-P | | | | | |
| Xyl-1-P | | | | | |
| β-L-Fuc-1-P | | | | | 0.00 |
| Man1-P | | | | | 20.37 |

TABLE 9

NUSSA
Enzyme: Crude extract, protein: 8.8 mg/ml
Source *Colpidium campylum*
Class: Ciliate
Specific activity (mU/mg)

| | UTP | CTP | dTTP | ATP | GTP |
|---|---|---|---|---|---|
| Glc-1-P | 500.00 | | | | |
| GlcN-1-P | 9.09 | | | | |
| GlcNAc-1-P | 92.05 | | | | |
| GlcA-1-P | | | | | |
| Gal-1-P | 112.50 | | | | |
| GalN-1-P | 13.64 | | | | |

TABLE 9-continued

| | |
|---|---|
| GalNAc-1-P | 79.55 |
| GalA-1-P | |
| Xyl-1-P | |
| β-L-Fuc-1-P | 129.55 |
| Man1-P | 65.91 |

TABLE 10

NUSSA
Enzyme: Filtrate, protein: 0.096 mg/ml
Source: *Colpidium campylum*
Class: Ciliate
Specific activity (mU/mg)

| | UTP | CTP | dTTP | ATP | GTP |
|---|---|---|---|---|---|
| Glc-1-P | 83.33 | | | | |
| GlcN-1-P | 0.00 | | | | |
| GlcNAc-1-P | 83.33 | | | | |
| GlcA-1-P | | | | | |
| Gal-1-P | 166.67 | | | | |
| GalN-1-P | 0.00 | | | | |
| GalNAc-1-P | 0.00 | | | | |
| GalA-1-P | | | | | |
| Xyl-1-P | | | | | |
| β-L-Fuc-1-P | | | | | 0.00 |
| Man1-P | | | | | 437.50 |

TABLE 11

NUSSA
Enzyme: Crude extract, protein: 42.5 mg/ml
Source: *Potomacus pottsi*
Class: Ciliate
Specific activity (mU/mg)

| | UTP | CTP | dTTP | ATP | GTP |
|---|---|---|---|---|---|
| Glc-1-P | 4.00 | | | | |
| GlcN-1-P | 0.50 | | | | |
| GlcNAc-1-P | 0.00 | | | | |
| GlcA-1-P | | | | | |
| Gal-1-P | 5.00 | | | | |
| GalN-1-P | 0.70 | | | | |
| GalNAc-1-P | 0.20 | | | | |
| GalA-1-P | | | | | |
| Xyl-1-P | | | | | |
| β-L-Fuc-1-P | | | | | 0.90 |
| Man1-P | | | | | 0.07 |

TABLE 12

NUSSA
Enzyme: Filtrate, protein: 0.11 mg/ml
Source: *Potomacus pottsi*
Class: Ciliate
Specific activity (mU/mg)

| | UTP | CTP | dTTP | ATP | GTP |
|---|---|---|---|---|---|
| Glc-1-P | 45.00 | | | | |
| GlcN-1-P | 4.50 | | | | |
| GlcNAc-1-P | 5.50 | | | | |
| GlcA-1-P | | | | | |

TABLE 12-continued

| | UTP | CTP | dTTP | ATP | GTP |
|---|---|---|---|---|---|
| Gal-1-P | 8.20 | | | | |
| GalN-1-P | 18.00 | | | | |
| GalNAc-1-P | 27.00 | | | | |
| GalA-1-P | | | | | |
| Xyl-1-P | | | | | |
| β-L-Fuc-1-P | | | | | 0.00 |
| Man1-P | | | | | 0.00 |

TABLE 13

NUSSA
Enzyme: Crude extract, protein: 12.8 mg/ml
Source: *Euglena gracilis*
Class: Phytomastigophorea
Specific activity (mU/mg)

| | UTP | CTP | dTTP | ATP | GTP |
|---|---|---|---|---|---|
| Glc-1-P | 323.44 | | | | |
| GlcN-1-P | 11.72 | | | | |
| GlcNAc-1-P | 43.75 | | | | |
| GlcA-1-P | | | | | |
| Gal-1-P | 46.88 | | | | |
| GalN-1-P | 0.00 | | | | |
| GalNAc-1-P | 49.22 | | | | |
| GalA-1-P | | | | | |
| Xyl-1-P | | | | | |
| β-L-Fuc-1-P | | | | | 75.00 |
| Man1-P | | | | | 69.53 |

TABLE 14

NUSSA
Enzyme: Filtrate, protein: 0.059 mg/ml
Source: *Euglena gracilis*
Class: Phytomastigophorea
Specific activity (mU/mg)

| | UTP | CTP | dTTP | ATP | GTP |
|---|---|---|---|---|---|
| Glc-1-P | 16.95 | | | | |
| GlcN-1-P | 0.00 | | | | |
| GlcNAc-1-P | 11.86 | | | | |
| GlcA-1-P | | | | | |
| Gal-1-P | 16.95 | | | | |
| GalN-1-P | 13.56 | | | | |
| GalNAc-1-P | 8.47 | | | | |
| GalA-1-P | | | | | |
| Xyl-1-P | | | | | |
| β-L-Fuc-1-P | | | | | 25.42 |
| Man1-P | | | | | 3.39 |

TABLE 15

Specific activities ≧ 50 mU/mg in the NUSSA.

| Sample | UDP-Glc | UDP-GlcN | UDP-GlcNAc | UDP-Gal | UDP-GalN | UDP-GalNAc | GDP-Fuc | GDP-Man |
|---|---|---|---|---|---|---|---|---|
| *Tetrahymena thermophila* | + | | + | + | | + | + | |
| *Euglena gracilis* | + | | + | + | | + | + | + |

TABLE 15-continued

Specific activities ≥ 50 mU/mg in the NUSSA.

| Sample | UDP-Glc | UDP-GlcN | UDP-GlcNAc | UDP-Gal | UDP-GalN | UDP-GalNAc | GDP-Fuc | GDP-Man |
|---|---|---|---|---|---|---|---|---|
| *Tetrahymena pyriformis* | + |  | + | + | + | + |  | + |
| *Colpidium campylum* | + |  | + | + |  | + | + | + |
| *Tetrahymena setosa* | + |  | + | + |  |  |  |  |

1 U is the enzyme activity which leads to production of 1 μmol of fructose 1,6-diphosphate per minute.

The invention claimed is:

1. An isolated nucleotide-sugar-synthesizing enzyme having the activity of GDP-fucose-pyrophosphorylase, obtained from a protist selected from the group consisting of *Tetrahymena thermophila, Tetrahymena setosa, Colpidium campylum, Potomacus pottsi* and *Euglena gracilis*.

2. The isolated nucleotide-sugar-synthesizing enzyme of claim 1 having the activity of GDP-fucose-pyrophosphorylase, obtained from *Tetrahymena setosa*.

3. The isolated nucleotide-sugar-synthesizing enzyme of claim 1 having the activity of GDP-fucose-pyrophosphorylase, obtained from *Colpidium campylum*.

4. The isolated nucleotide-sugar-synthesizing enzyme of claim 1 having the activity of GDP-fucose-pyrophosphorylase, obtained from *Potomacus pottsi*.

5. The isolated nucleotide-sugar-synthesizing enzyme of claim 1 having the activity of GDP-fucose-pyrophosphorylase, obtained from *Euglena gracilis*.

6. The isolated nucleotide-sugar-synthesizing enzyme of claim 1 having the activity of GDP-fucose-pyrophosphorylase, obtained from *Tetrahymena thermophila*.

* * * * *